United States Patent [19]

Bowman et al.

[11] Patent Number: 4,996,363

[45] Date of Patent: Feb. 26, 1991

[54] CATALYTIC REFORMING OF ALKYLENEAMINES TO LINEARLY-EXTENDED POLYALKYLENEPOLYAMINES

[75] Inventors: Robert G. Bowman; David C. Molzahn; George E. Hartwell, all of Midland, Mich.

[73] Assignee: The Dow Chemical Company, Midland, Mich.

[21] Appl. No.: 287,189

[22] Filed: Dec. 20, 1988

[51] Int. Cl.$^5$ .................. C07C 209/64; C07C 211/14; C07D 295/13; C07D 295/023

[52] U.S. Cl. ................................. 564/470; 564/469; 564/511; 564/512; 544/358; 544/402

[58] Field of Search ............... 564/469, 512, 470, 511; 544/358, 402

[56] References Cited

U.S. PATENT DOCUMENTS

| | | | |
|---|---|---|---|
| T945,004 | 8/1976 | Valaitis et al. | 260/2 R |
| 2,414,552 | 2/1947 | Pfann et al. | 260/250 |
| 2,454,404 | 2/1948 | Pfann et al. | 260/268 |
| 3,297,700 | 1/1967 | Muhlbauer et al. | 260/268 |
| 3,956,329 | 4/1976 | Murakami et al. | 260/268 SY |
| 4,206,150 | 5/1980 | Slaugh | 260/583 R |
| 4,316,840 | 2/1982 | Ford et al. | 260/239 BC |
| 4,316,841 | 1/1982 | Ford et al. | 260/239 BC |
| 4,495,369 | 1/1985 | Werner et al. | 564/480 |
| 4,524,143 | 2/1985 | Vanderpool | 502/208 |
| 4,547,591 | 10/1985 | Brennan et al. | 564/479 |
| 4,562,291 | 4/1985 | Wilson, Jr. et al. | 564/463 |
| 4,568,746 | 2/1986 | Cowherd, III | 544/358 |
| 4,625,030 | 1/1986 | Best | 544/358 |
| 4,736,030 | 4/1988 | Mueller et al. | 544/374 |

FOREIGN PATENT DOCUMENTS

| | | |
|---|---|---|
| 0256516 | 2/1988 | European Pat. Off. |
| 2719718.8 | 11/1978 | Fed. Rep. of Germany |
| 2736759.5 | 3/1979 | Fed. Rep. of Germany |
| 2147896 | 5/1985 | United Kingdom |

OTHER PUBLICATIONS

Piperazin, Akademianauk Latv. SSR, S. A. Giller and M. V. Shimanskaya, eds., 1965, pp. 41–54. (Russian copy and English language translation enclosed).
Doklady Akademii Nauk SSSR, 169(6), 1332 (1966), (Translation enclosed).
Latvijas PSR Zinatnu Akademijas Vestis, Kimijas Serije, 1971(1), 47–58, (Translation enclosed).
Chemical Abstracts 84:164140f (1976).
Chemical Abstracts 82:156378h (1975).
Chemical Abstracts 101:229978b (1984).
Derwent 86-163138/26 (1986).
Chemical Abstracts 32:5414$^9$ (1932).
Chemical Abstracts 69:67422g (1968).
Chemical Abstracts 66:28325w (1967).
Chemical Abstracts 66:28327y (1967).
Khimiya Geterotsiklicheskikh Soedinenii, 1967(2), 346–359, (Translation enclosed).
Chemical Abstracts 73:109263w (1970).

*Primary Examiner*—Robert T. Bond
*Assistant Examiner*—Peter G. O'Sullivan

[57] ABSTRACT

A process for reforming alkyleneamines to predominantly linearly-extended polyalkylenepolyamines comprising contacting an alkyleneamine or mixture thereof with a catalyst under conditions such that a mixture of polyalkylenepolyamines enriched in linearly-extended products is formed, said catalyst containing at least one compound selected from the group consisting of (a) Group VB metal oxides, (b) Group VB metal phosphates, (c) silicates of Groups IIA, IIIB, IVB, VB, and the lanthanide and actinide metals, and (d) tungsten oxides, with the proviso that the silicates and tungsten oxides are essentially free of aluminum. For example, ethylenediamine is contacted with a catalyst of niobium phosphate or niobic acid under reaction conditions to yield predominantly non-cyclic polyethylenepolyamines.

23 Claims, No Drawings

CATALYTIC REFORMING OF ALKYLENEAMINES TO LINEARLY-EXTENDED POLYALKYLENEPOLYAMINES

BACKGROUND OF THE INVENTION

This invention relates to a process for preparing linearly-extended polyalkylenepolyamines, such as diethylenetriamine, and linear and branched triethylenetetramines.

Linearly-extended polyalkylenepolyamines find utility as dispersants, surfactants, chelants, catalysts, curing agents, extenders in polyurethanes, and as starting materials in the preparation of pesticides.

It is known that non-cyclic polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. The neutralization produces a waste stream of metal salt which must be removed. Moreover, the process produces considerable amounts of undesirable cyclic products.

Certain patents teach the reforming of alkylenepolyamines, such as ethylenediamine, directly to non-cyclic polyalkylenepolyamines. For example, U.S. Pat. No. 4,316,841 discloses such a process with a catalyst of boron phosphate, a phosphate of a Group IA or IIA metal, or a phosphate of zirconium, antimony, tin or iron. These catalysts are soluble in amines and water. Consequently, they leach into the reaction causing catalyst losses and separation problems.

U.S. Pat. No. 3,956,329 discloses the deammoniation of an alkyleneamine or an aminoethylpiperazine over a zeolite catalyst containing at least one cation selected from the alkali metals, the alkaline earth metals, zinc group elements, hydrogen and ammonium cations. Disadvantageously, this process produces large amounts of undesirable cyclic materials, such as triethylenediamine and piperazine.

U.S. Pat. No. 4,547,591 discloses the preparation of predominantly linear polyethylenepolyamines by reforming ethyleneamines in the presence of a silica-alumina catalyst. Optionally, the catalyst contains an acidic phosphorus cocatalyst. This process produces considerable quantities of undesirable cyclic materials, such as piperazines.

U.S. Pat. No. 4,568,746 teaches a process of reforming ethylenediamine in the presence of a catalyst containing nickel, cobalt or rhodium. Likewise, U.S. Pat. No. 4,625,030 teaches a process of contacting ethylenediamine in the presence of hydrogen with a catalyst comprising nickel impregnated or coated together with iridium or platinum on a support of silica-alumina. These processes are limited to the preparation of diethylenetriamine, and do not produce higher homologues. Moreover, these processes require hydrogen and an expensive noble metal.

It would be desirable to have an inexpensive catalyst which is capable of reforming alkylenepolyamines directly to polyalkylenepolyamines without the formation of undesirable by-products, such as water. It would be more desirable if such a catalyst was insoluble in amines and water, so as to avoid catalyst losses and separation problems. It would be most desirable if the catalyst produced high yields of linearly-extended polyalkylenepolyamines, and simultaneously low yields of undesirable cyclic products.

SUMMARY OF THE INVENTION

This invention is a process for reforming an alkyleneamine comprising contacting an alkyleneamine or mixture thereof with a catalyst under reaction conditions such that a mixture of polyalkylenepolyamines is produced which is enriched in linearly-extended homologues. The catalyst which is employed in the reforming process of this invention contains at least one compound selected from the group consisting of:

(a) Group VB metal oxides:
(b) Group VB metal phosphates:
(c) silicates of Groups IIA, IIIB, IVB, VB, and the lanthanide and actinide metals, and
(d) tungsten oxides, with the proviso that the silicates and tungsten oxides are essentially free of aluminum.

Advantageously, the process of this invention converts alkyleneamines directly to polyalkylenepolyamines Thus, the process of this invention does not require the neutralization of hydrohalide salts and the disposal of a waste metal salt stream. More advantageously, the process of this invention does not produce water as a by-product. Even more advantageously, the catalysts of this process are insoluble in water and amines: therefore, catalyst losses are minimized, and the separation of products from the catalyst is relatively easy. Moreover, the catalysts employed in the process of this invention are inexpensive when compared with the noble metal catalysts of the prior art. Most advantageously, the process of this invention gives a high selectivity to linearly-extended polyalkylenepolyamines and simultaneously a low selectivity to undesirable cyclic products.

The linearly-extended polyalkylenepolyamine products of this invention are useful as dispersants, surfactants, curing agents, chelants, and catalysts, and are also useful in the formation of urethane polymers, ureas, and pesticides.

DETAILED DESCRIPTION OF THE INVENTION

The alkyleneamines which are employed in the process of this invention include any alkylene moiety containing at least two primary and/or secondary amine functionalities. The alkylene component of the alkyleneamines can be straight or branched, substituted or unsubstituted. If substituted, the substituent should be inert. For the purposes of this invention the term "inert" means that the substituent is non-reactive in the reforming process and with the polyalkylenepolyamine products. Such inert substituents include alkyl moieties and aryl moieties. Preferably, the inert substituent is a $C_1$–$C_{12}$ alkyl moiety, such as methyl, ethyl, propyl, or butyl, or a monocyclic aryl moiety, such as phenyl or tolyl. Several examples of suitable alkyleneamines include ethylenediamine, propylenadiamine, diethylenetriamine, linear and branched triethylenetetramines, and analogous higher homologs of ethylenepolyamine and propylenepolyamine: as well as polyether alkyleneamines such as 2-($\beta$-aminoethoxy)aminoethane, 1,4-bis($\beta$-aminoethoxy)butane, and 1,4-bis($\gamma$-aminopropoxy)butane. Mixtures of any of the aforementioned compounds are also acceptable. While the above-identified alkyleneamines are representative of those which can be employed in the process of this invention, other alkyleneamines may be found which are equally suitable.

The preferred alkyleneamines can be represented by the general formula:

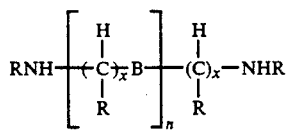

wherein each B is independently NR or O; each R is independently hydrogen, amino, a $C_1$-$C_{12}$ alkyl moiety such as methyl, ethyl, or propyl, a $C_1$-$C_{12}$ aminoalkyl moiety, or a monocyclic aromatic moiety, such as phenyl or tolyl; each x is independently a number from 1 to about 12; and n is a number from 0 to about 150. Preferably, each B is NR. More preferably, each B is NR and each R is hydrogen. Even more preferably, each B is NR, each R is hydrogen, x is 2, and the alkyleneamine is ethylenediamine or an oligomer thereof. Most preferably, the alkyleneamine is ethylenediamine.

Although it is preferred to carry out the amination reaction in the absence of solvent, it is within the scope of the invention for a solvent to be used, if desired. Any solvent is acceptable provided that (1) it is not reactive with the alkyleneamine reactants and polyalkylenepolyamine products, and (2) it does not decompose under the conditions of the reaction Some examples of suitable solvents include saturated aliphatic hydrocarbons such as pentane, hexane, octane, nonane, and decane, and aromatic hydrocarbons such as benzene, toluene, and xylene. If necessary, water can be employed as a solvent. The amount of solvent employed in the reaction depends on the particular reactants and reaction conditions. Any amount of solvent is acceptable that meets the intended purpose of use. Typically, the solvent constitutes from about 5 weight percent to about 95 weight percent of the feed stream. Preferably, the solvent constitutes from about 10 weight percent to about 80 weight percent of the feed stream.

A variety of catalysts can be employed in the reforming process of this invention including (a) Group VB metal oxides, (b) Group VB metal phosphates, (c) silicates of Groups IIA, IIIB, IVB, VB, and the lanthanide and actinide metals, and (d) tungsten oxides, with the proviso that the silicates and tungsten oxides are essentially free of aluminum. These catalysts can be employed in the reforming process singly or in combination with any other of said catalysts. A detailed description of each catalyst group is given hereinafter.

A. Group VB Metal Oxides

Group VB metal oxides are suitably employed as catalysts in the reforming process of this invention. The Group VB elements include vanadium (V), niobium (Nb), and tantalum (Ta). Examples of suitable Group VB metal oxides include vanadium oxides such as VO, $VO_2$, $V_2O_3$, $V_2O_5$, $V_3O_5$, $V_5O_9$, $V_6O_{13}$; niobium oxides such as NbO, $NbO_2$, $Nb_2O_5$; tantalum oxides such as $Ta_2O_5$; as well as hydrated oxides including vanadates such as $H_3VO_4$, niobic acids such as $Nb_2O_5.xH_2O$, $H_8Nb_6O_{19}.xH_2O$, and $[H_2Nb_6O_{16}]_m$, tantalic acid, and mixtures of Group VB metal oxides and/or hydrated metal oxides. Non-stoichiometric oxides are also suitable. Preferably, the Group VB metal is in the +3 or +5 oxidation state. More preferably, the Group VB metal oxide is an oxide or hydrated oxide of niobium. Most preferably, the Group VB metal oxide is a hydrated niobium oxide.

Generally, the common Group VB metal oxides are commercially available; while the less common oxides can be prepared by methods known in the art. The preparation of some less common Group VB metal oxides can be found in *Comprehensive Inorganic Chemistry*, op. cit., pp. 510–524 and 592–599.

B. Group VB Metal Phosphates

A Group VB metal phosphate can be suitably employed as a catalyst in the reforming process of this invention. As noted hereinbefore, the Group VB metals include vanadium, niobium, and tantalum. Examples of suitable Group VB metal phosphate compounds include vanadium phosphates such as $V_2O_5.P_2O_5$; niobium phosphates such as $2Nb_2O_5.P_2O_5.6H_2O$, $2Nb_2O_5.P_2O_5$, $NbOPO_4$, $PNb_9O_{25}$; and tantalum phosphates such as $2Ta_2O_5.P_2O_5$, $2Ta_2O_5P_2O_56H_2O$, $TaOPO_4$. Group VB metal meta-phosphates, fluorophosphates, hydrated phosphates, and non-stoichiometric phosphate compounds are also suitable, as are Group VB metal hydrogen phosphates. Preferably, the Group VB metal phosphate possesses a P/metal mole ratio no greater than about 3.0. More preferably, the Group VB metal phosphate possesses a P/metal mole ratio no greater than about 1.0. Most preferably, the Group VB metal phosphate possesses a P/metal mole ratio in the range from about 0.02 to about 1.0. Preferably, the Group VB metal phosphate is a niobium phosphate, more preferably, $NbOPO_4$ or the hydrated forms of $NbOPO_4$.

The Group VB metal phosphates are relatively easy to prepare. The preparations are described in *Comprehensive Inorganic Chemistry*. Vols. 1–5, J. C. Bailar, Jr., H. J. Emeleus, R. Nyholm, and A. F. Trotman-Dickenson, eds., Pergamon Press, Oxford (1973) pp. 612–613, and references cited therein. Preferably, the Group VB metal phosphate catalyst is prepared by reacting a catalyst precursor compound containing a Group VB metal with a phosphorus-containing compound, such as phosphoric acid, under conditions sufficient to generate the Group VB metal phosphate. Typical catalyst precursor compounds which can be employed as starting materials include Group VB metal oxides, hydrated oxides, halides, alkoxides, and carboxylic acid salts. Anhydrous or aqueous phosphoric acid can be employed, as can fluorinated phosphoric acids, or fluorinated phosphorus-containing compounds. The phosphoric acid is typically employed as an 85 weight percent aqueous solution; however, additional water can be used to obtain Group VB metal phosphate compounds having higher surface area. More specifically, the catalyst precursor, such as a Group VB metal oxide, is heated with phosphoric acid at about atmospheric pressure and at a temperature in the range from about 130° C. to about 200° C. The weight ratio of phosphoric acid to precursor compound is preferably in the range from about 5 to about 20, more preferably, in the range from about 7 to about 15, most preferably, about 10. The length of time the precursor compound and phosphoric acid are heated varies depending upon the quantity of precursor compound employed and quantity of by-products which are driven off during heating. Typically, however, the mixture is heated for about one to two hours; however, longer times may be employed. After heating, the mixture which comprises a liquid phase and a solid phase is cooled. The liquid is decanted from the solid, and the solid is washed with water and filtered. The washing and filtering may be repeated several times to ensure the removal of excess acid and unwanted ions. The filtered solid is dried at a temperature in the range from about 80° C. to about 150° C. in air for a time in the range from about 2 hours to about 50 hours to yield the Group VB metal phosphate. Typically, the metal phosphate compound is heat treated or calcined prior to use. Preferably, the calcination is conducted at a temperature in the range from about 200° C. to about 500° C. for a time in the range from about 2 hours to about 50 hours.

C. Silicates of Groups IIA, IIIB, IVB, VB, and the Lanthanide and Actinide Metals In accordance with the process of this invention, the reforming reaction can be conducted in the presence of a catalyst comprising a metal silicate. The metal silicate is any silicate of Groups IIA, IIIB, IVB, VB, and the lanthanide and actinide metals. Preferably, the metal of the metal silicate is beryllium, magnesium, calcium, strontium, barium, actinium, thor, protactinum, uranium, scandium, yttrium, lanthaium num, titanium, zirconium, hafnium, vanadium, niobium, or tantalum. More preferably, the metal of the metal silicate is magnesium, titanium, niobium, thorium, or yttrium. Most preferably, the metal of the metal silicate is magnesium or thorium. The metal silicate can be employed in an amorphous form containing a distribution of silicate anions of various sizes. Alternatively, the metal silicate can be employed in a crystalline form, such as the siliceous zeolite structure exhibited by sodium magnesium silicate.

It is required that the metal silicate catalyst employed in the process of this invention be essentially free of aluminum. The term "essentially free of aluminum" means that the metal silicate contains less than about 5 weight percent aluminum. Preferably, the metal silicate contains less than about 2 weight percent aluminum, more preferably, less than about 1 weight percent aluminum.

The mole ratio of silicon to metal will vary in the metal silicate depending upon the metal cation, its valence, and the form of the silicate anion. For instance, in the case of magnesium silicate, the preferred silicon to magnesium mole ratio varies from about 0.5 to about 20. More preferably, the silicon to magnesium mole ratio varies from about 1 to about 10, most preferably, from about 1 to about 5. Other metal silicates may exhibit silicon to metal mole ratios which are different from the preferred ratios shown here for magnesium silicate.

The common metal silicates which are employed in the process of this invention are commercially available. The less common silicates, such as thorium silicate and other metal silicates, may be prepared by methods reported in *The Colloid Chemistry of Silica and Silicates* by Ralph K. Iler, Cornell University Press, 1955: or in *The Chemistry of Silica: Solubility, Polymerization, Colloid and Surface Properties, and Biochemistry* by Ralph K. Iler, John Wiley & Sons, 1979: and references therein.

The metal silicate catalyst can be prepared by a variety of synthetic methods. One, for example, requires the formation of a mixture of silica ($SiO_2$) with the oxide of the desired metal. The oxide mixture is calcined at a temperature sufficient to form the desired metal silicate. Another method, for example, depends upon the hydrolysis of mixtures of tetra(ethoxy)silicon and an alkoxide of the desired metal, e.g., tetra(methoxy)titanium. The hydrolysis reaction yields the desired metal silicate.

Preferably, however, the metal silicates are prepared by direct precipitation from a mixture of two aqueous solutions. One of these solutions contains a soluble silicate salt, such as sodium silicate. Typically, the soluble silicate salt is dissolved in a minimum amount of water. Typically, the solution is heated, preferably to boiling, to aid in the dissolution of the salt. Optionally, the aqueous silicate solution can be acidified with strong acid, such as nitric acid, in order to prepare larger silicate anions, such as $Si_2O_5^{2-}$ or $Si_3O_7^{2-}$. Similarly, a soluble metal compound containing the desired metal ion is dissolved in a minimum amount of water to make a second solution. The soluble metal compound can be, for example, a metal nitrate, such as magnesium nitrate, calcium nitrate, or lanthanum nitrate: a metal chloride, such as yttrium chloride: or the like. Likewise, the second solution is heated to boiling to facilitate dissolution of the soluble metal compound. The two solutions are mixed and a precipitate forms of the desired metal silicate catalyst. The catalyst is filtered and dried by known methods.

D. Tungsten Oxides

Tungsten oxides are also suitably employed in the reforming process of this invention. The tungsten oxides can be simple mononuclear tungsten oxides, which are compounds containing only one tungsten atom, such as ammonium tungstate. Alternatively, the tungsten oxides can be multinuclear tungsten clusters, which are compounds containing a plurality of tungsten atoms, such as $(NH_4)_{10}(W_{12}O_{41})$. In addition, it is preferred that the tungsten be in the $+4$, $+5$, or $+6$ oxidation state. Examples of suitable tungsten oxides include $WO_2$, $WO_3$, $(NH_4)_2WO_4$, para-ammonium tungstate, $H_2(W_6O_{19})$, $[(n-C_4H_9)_4N]_2(W_6O_{19})$, $(NH_4)_{10}(W_{12}O_{41})$ $(NR_4)_2(W_6O_{19})$ and $(NR_4)_4(W_{10}O_{32})$, wherein R is H or an alkyl moiety; however, the tungsten oxides are not limited to only the aforementioned examples. The preferred mononuclear tungsten oxide compounds have the general formula:

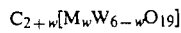

wherein C is a monovalent cation, such as Na+, K+, H+, or a quaternary ammonium salt, NR4+, wherein R is H or an alkyl moiety such as butyl or propyl, w is an integer from 0 to 3, and M is vanadium (V), niobium (Nb), or tantalum (Ta). Preferably, C is tetrabutylammonium ($+1$).

It is required that the tungsten oxide catalyst employed in the process of this invention be essentially free of aluminum. The term "essentially free of aluminum" means that the tungsten oxide contains less than about 5 weight percent aluminum. Preferably, the tungsten oxide contains less than about 2 weight percent aluminum, more preferably, less than about 1 weight percent aluminum. The more common of the tungsten oxides, such as $WO_2$, $WO_3$, $(NH_4)_2WO_4$, and para-ammonium tungstate can be purchased commercially from Alfa Products or Aldrich. The less common oxides and cluster compounds can be prepared by methods described in *Comprehensive Inorganic Chemistry*, Vol. 3, J. C. Bailar, Jr., H. J. Emeleus, R. Nyholm, and A. F. Trotman-Dickenson, eds., Pergamon Press Ltd., Oxford (1973) pp. 763-769: and in "Isopolytungstates" by D. L. Keperl in *Progress in Inorganic Chemistry*, Vols. 4, Intersciences Press, New York (1962) p. 199. The preparation of $[(n-C_4H_9)_4N]_2(W_6O_{19})$ and various polyoxometalates is reported by M. Filowitz, R. K. C. Ho, W.

G. Klemperer, and W. Shum in *Inorganic Chemistry*, 18, no.1, 93–103 (1979), and by V. W. Day, W. G. Klemperer and C. Schwartz in the *Journal of the American Chemical Society*, 109 No. 20, 6030–6044 (1987).

It is preferred that the aforementioned catalysts (A–D) are insoluble in the reforming reaction mixture, thereby acting as heterogeneous catalysts. Optionally, any of the catalysts can be made insoluble by (a) depositing onto a support material, or (b) binding with a refractory metal oxide or a support precursor. Any support or binder material is acceptable provided that it does not enhance the formation of undesirable cyclic products in the reforming process of this invention. Suitable supports or binders include carbon and any refractory oxide such as alumina (hydrated and dehydrated forms), silica, zirconia, thoria, magnesia, titania, kielselguhr, and mixtures of these materials. Suitable support precursors include hydrated metal oxides and metal alkoxides. Preferably, the support or binder material is alumina, silica or titania. The support material typically has a surface area of at least about 0.1 m$^2$/g. Preferably, the support material has a surface area in the range from about 5 m$^2$/g to about 600 m$^2$/g, most preferably in the range from about 50 m$^2$/g to about 200 m$^2$/g. These surface areas are measured by the Brunauer-Emmett-Teller (BET) method, as described by R. B. Anderson, in *Experimental Methods in Catalytic Research*, Academic Press (1968) pp. 48–66.

The catalyst compounds can be deposited onto the support material in any known fashion, such as by impregnation or by precipitation in situ from the catalyst preparation reaction. In these types of preparation the catalyst is adsorbed onto the support. Alternatively, the catalyst can be chemically reacted onto the support. In this method a catalyst precursor compound is reacted with the hydroxyl functionalities of the support to yield a catalyst precursor chemically bound to the support. The bound catalyst precursor can then be converted into the Group VB or VIB metal oxide catalyst by hydrolysis or heating. Similarly, the bound catalyst precursor can be converted into the Group VB phosphate catalyst of the invention by reaction with phosphoric acid. For example, niobium chloride reacts with the hydroxyl moieties of silica to yield niobium chloride bound through an oxygen to silicon. The bound niobium chloride can be heated to yield a bound niobium oxide catalyst, or reacted with phosphoric acid to yield a bound niobium phosphate catalyst.

The amount of catalyst, which is employed in the process of this invention, is any amount which is effective in producing the desired linearly-extended polyalkylanepolyamine products. The amount of catalyst varies widely depending upon the specific reactants and process conditions employed. Typically, for a batch reaction the quantity of catalyst is in the range from about 0.1 weight percent to about 20 weight percent based on the weight of reactant alkyleneamine. Preferably, the amount of catalyst is in the range from about 1 weight percent to about 15 weight percent based on the weight of reactant alkyleneamine.

The process of this invention can be conducted in any suitable reactor, including batch reactors, continuous fixed-bed reactors, slurry reactors, fluidized bed reactors, and catalytic distillation reactors. Preferably, the reactor is a continuous fixed-bed reactor.

The alkyleneamine or mixture thereof is contacted with the catalyst at any operable temperature which promotes the reforming reaction and produces the desired linearly-extended polyalkylenepolyamine products. Typically, the temperature is in the range from about 200° C. to about 400° C. Preferably, the temperature is in the range from about 250° C. to about 350° C. More preferably, the temperature is in the range from about 260° C. to about 315° C. Below the preferred lower temperature the conversion of alkyleneamine may be low. Above the preferred upper temperature the selectivity for linearly-extended polyalkylenepolyamines may decrease.

Likewise, the alkyleneamine reactant is contacted with the catalyst at any operable pressure which promotes the reforming reaction and produces the desired linearly-extended polyalkylenepolyamine products. Preferably, the pressure is sufficient to maintain the reactants in the liquid stata at the temperature of the reaction. More preferably, the pressure is in the range from about atmospheric to about 4000 psig. Even more preferably, the pressure is in the range from about 500 psig to about 3000 psig. Most preferably, the pressure in the range from about 1000 psig to about 2000 psig. In batch reactors the pressure is autogenous, and depends upon the vapor pressures of the reactants and products and the temperature of the reaction.

When the process of this invention is conducted in a continuous flow reactor, the flow rate of the reactants can be varied. Generally, the alkyleneamine, or mixture thereof, and any solvent are premixed to form a feed stream which is fed into the reactor at any operable flow rate which allows for reaction to predominantly linearly-extended polyalkylenepolyamine products. The flow rate is expressed as the liquid hourly space velocity and is given in units of grams of total reactants per milliliter of total reactor volume per hour, g ml$^{-1}$ hr$^{-1}$. It is preferred to employ a liquid hourly space velocity in the range from about 0.1 g ml$^{-1}$ hr$^{-1}$ to about 10.0 g ml$^{-1}$ hr$^{-1}$ more preferably in the range from about 0.5 g ml$^{-1}$ hr$^{-1}$ to about 4.0 g ml$^{-1}$ hr$^{-1}$. It is understood that the liquid hourly space velocity controls the residence time of the reactants in the continuous flow reactor.

When the process of this invention is conducted in a batch reactor, the reaction time determines the length of contact between the reactants and the catalyst. Any reaction time which yields the desired linearly-extended polyalkylenepolyamine products is acceptable. The reaction time depends upon the quantity of reactants, the quantity of catalyst, the temperature of the reaction and desired degree of conversion. Preferably, the reaction time in a batch reactor is in the range from about 1 hour to about 20 hours.

When the alkyleneamine is contacted with at least one of the catalysts described hereinbefore, the alkyleneamine is reformed into polyalkylenepolyamine products. Ammonia is eliminated as a by-product. Typically, the molecular weight of the polyalkylenepolyamine products is greater than the molecular weight of the alkyleneamine reactant. Preferably, the product is a mixture of polyalkylenepolyamines enriched in linearly-extended or non-cyclic homologues. For example, if the reactant is ethylenediamine, the preferred polyalkylenepolyamines are diethylenetriamines and linear and branched triethylenetetramines. In addition to linearly-extended products, undesirable cyclic products containing new N-heterocycles may be formed. Piperazine and 1,4-diaza-[2.2.2]-bicyclooctane are examples of an undesirable cyclic products.

The preferred linearly-extended polyalkylenepolyamine products can be represented by the general formula:

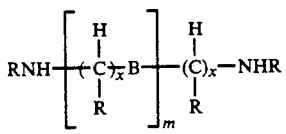

wherein m is a positive number from 1 to about 300, and R, B and x are defined hereinbefore. Preferably, each B is NR. More preferably, each B is NR and each R is hydrogen. Even more preferably, each B is NR, each R is hydrogen, and x is 2. Most preferably, each B is NR, each R is hydrogen, x is 2, and m is 1, 2, or 3: and the polyalkylenepolyamines are diethylenetriamine, triethylenetetramine, and tetraethylenepentamine.

For the purposes of this invention "conversion" is defined as the weight percentage of alkyleneamine reactant lost as a result of reaction. The conversion varies widely depending upon the reactants, the form of the catalyst, and the process conditions, such as temperature, pressure, and flow rate. Within the preferred temperature range, as the temperature increases the conversion generally increases. Within the preferred space velocity range, as the space velocity increases the conversion generally decreases. Typically, the conversion of the alkyleneamine is at least about 3 weight percent. Preferably, the conversion is at least about 10 weight percent: more preferably at least about 20 weight percent: even more preferably at least about 30 weight percent: and most preferably, at least about 45 weight percent.

Likewise, for the purposes of this invention "selectivity" is defined as the weight percentage of converted alkyleneamine which forms a particular polyalkylenepolyamine product. Typically, the selectivities also vary widely depending upon the reactants, the form of the catalyst, and the process conditions. Typically, the process of this invention achieves high selectivities to linearly-extended polyalkylenepolyamines. Within the preferred temperature range as the temperature increases, the selectivity for linearly-extended polyalkylenepolyamines generally decreases. Within the preferred space velocity range as the space velocity increases, the selectivity for linearly-extended polyalkylenepolyamines increases. Preferably, the combined selectivity to all linearly-extended polyalkylenepolyamines is at least about 45 weight percent: more preferably, at least about 60 weight percent, even more preferably, at least about 75 weight percent, and most preferably, at least about 85 weight percent.

Where applicable, the efficiency of the reforming reaction in forming linearly-extended products can be measured by calculating the diethylenetriamine/piperazine weight ratio, abbreviated DETA/PIP. The higher the value of this ratio, the more linearly-extended polyalkylenepolyamines are present in the product mixture. Preferably, the DETA/PIP weight ratio is at least about 3. More preferably, the DETA/PIP weight ratio is at least about 10: most preferably, at least about 20. Another measure of the efficiency of the reaction in forming linearly-extended products is the weight percentage of triethylenetetramines which are non-cyclic, % NC TETA. Preferably, % NC TETA is at least about 50 weight percent. More preferably, % NC TETA is at least about 70 weight percent: most preferably, at least about 90 weight percent. A third measure of the efficiency of the reaction in forming linearly-extended products is the weight percentage of tetraethylenepentamines which are non-cyclic, % NC TEPA. Preferably, % NC TEPA is at least about 50 weight percent. More preferably, % NC TEPA is at least about 70 weight percent: most preferably, at least about 90 weight percent.

The following examples are illustrative of the invention: but, are not intended to be limiting thereof. All percentages are given in weight percent, unless noted otherwise. In some instances the following abbreviations are used to indicate the reactants and products:

| EDA | ethylenediamine |
|---|---|
| AEEA | N-(2-aminoethyl)ethanolamine |
| DETA | diethylenetriamine |
| TETA | triethylenetetramine |
| TEPA | tetraethylenepentamine |
| PEHA | pentaethylenehexamine |
| PIP | piperazine |
| AEP | N-(2-aminoethyl)piperazine |

EXAMPLE 1

(a) Preparation of Niobium Phosphate Catalyst

Niobic acid, $Nb_2O_5xH_2O$ (60.33 g: 0.211 mole) is stirred in 85 percent phosphoric acid (602.20 g: 5.22 moles) at 150° C. The niobium oxide dissolves to form a pink solution, and upon further heating a precipitate forms. The precipitate is boiled in the phosphoric acid solution for about 2 hours with stirring. The mixture is cooled to room temperature, and the liquid is decanted from the precipitate. Water (500 ml) is added to the precipitate with stirring, and the precipitate is filtered. The washing and filtering cycle is repeated five times. The filtered solid is dried at 110° C. under air for 2½ days to yield a niobium phosphate catalyst. The elemental analysis of the catalyst is consistent with the composition $NbOPO_4$.

(b) Reforming of Ethylenediamine

Ethylenediamine (25 g, 0.42 mole) and the niobium phosphate catalyst (1.0 g), prepared hereinabove, are loaded into a 300-cc glass-lined, stirred autoclave. The reactor is purged with nitrogen, heated to 300° C., and held at that temperature for nine hours. After cooling to room temperature the liquid products are analyzed by gas-liquid chromatography. A CAM (Carbowax amine deactivated) capillary column (15 m×0.25 mm dia.) is employed for the analysis of total amine products. Isomer distributions are determined on an SE-54 capillary column (30 m×0.25 mm dia.). The following results are obtained: conversion of EDA, 26 percent: selectivities on a feed-free basis to DETA, 58.3 percent: TETA, 11.4 percent: TEPA, 4.0 percent: PIP, 4.8 percent: and AEP, 3.7 percent. The DETA/PIP ratio is 12.1. The data show that niobium phosphate catalyzes the reforming of ethylenediamine to predominantly linearly-extended polyethylenepolyamines.

EXAMPLE 2

Niobic Acid, $Nb_2O_5.xH_2O$ (23.0 g, Niobium Products Corp., CBMM number AD 222) is pressed at 20,000 psi into cylindrical pellets 1 inch in diameter by 1 inch in length. Each pellet contains approximately 25 grams niobic acid. The pressed pellets are dried at 120° C. for 4 hours. The dried pellets are heated slowly under air to a temperature of 300° C. and calcined overnight at that temperature. The catalyst pellets are crushed and sieved to 14-20 mesh prior to use in the reactor. The sieved catalyst is packed into a fixed-bed reactor, and a feed comprising diethylenetriamine, alone or in mixture with ethylenediamine, is passed through the catalyst bed at a variety of reaction temperatures, pressures, and flow rates with the results presented in Table I.

is 20 percent and the selectivities are the following: EDA, 14 percent: TETA, 15 percent: TEPA, 52 percent: PEHA, 4 percent; PIP, 8 percent: AEP, 7 percent. The % NC TETA is 77 percent, and the % NC TEPA is 94 percent. The data show that silica-supported tungsten oxide catalyzes the reforming of diethylenetriamine to predominantly linearly-extended higher polyathylenepolyamines.

TABLE I

| Ex. 2 [1] | Temp (°C.) | P psig | LHSV g per ml-hr | % Conv. DETA | EDA | TETA (% NC TETA) [3] | TEPA (% NC TEPA) [3] | PEHA | PIP | AEP |
|---|---|---|---|---|---|---|---|---|---|---|
| a | 280 | 1188 | 2.3 | 16 | — | 50 (99+) | 17 (99+) | 9 | 16 | 7 |
| b | 310 | 1188 | 2.3 | 37 | — | 42 (89) | 26 (89) | 4 | 18 | 9 |
| c | 285 | 1405 | 5.1 | 14 | 16 | 19 (84) | 43 (99+) | tr | 14 | 7 |
| d | 290 | 1253 | 1.4 | 47 | 16 | 21 (70) | 35 (93) | 5 | 16 | 7 |
| e | 315 | 1317 | 1.3 | 64 | 19 | 23 (59) | 30 (79) | 7 | 12 | 8 |

% Selectivity (feed-free basis) [2]

[1] Feedstream comprises (a-b) DETA and EDA in an EDA/DETA mole ratio of 2, and (c-e) DETA alone.
[2] % Selectivity is the weight percentage of specific product, based on the total weight of the product stream less the weight in the product stream of the feed component(s).
[3] (% NC TETA) and (% NC TEPA) are the weight percentages of triethylenetetramines and tetraethylenepentamines, respectively, which are non-cyclic.

It is seen that niobic acid catalyzes the reforming of diethylenetriamine, alone and in mixtures with ethylenediamine, to predominantly linearly-extended higher polyethylenepolyamines. Moreover, below about 50 percent conversion, the selectivity to non-cyclic tetraethylenepentamine is very high.

EXAMPLE 3

(a) Preparation of Silica-Supported Ammonium Tungstate

Para-ammonium tungstate (15.0 g: Amends Chemical Company) is added to 400 ml of water to which 5 ml of 30 percent hydrogen peroxide are added. The resulting mixture is heated with stirring at 80° C.-90° C. for 60 minutes to form a solution. The solution is cooled to room temperature and added to a flask containing silica (25.0 g: Shell Silica Spheres S-980: 1.5 mm dia.). Water is removed from the silica mixture by rotary evaporation. The resulting solid is dried in a muffle furnace at 350° C. overnight to form a silica-supported tungsten oxide catalyst.

(b) Reforming of Diethylenetriamine

The supported tungsten oxide catalyst (7.9 g), prepared hereinabove, is used to reform diethylenetriamine according to the general procedure of Example 2. At a temperature of 315° C., a pressure of 1405 psig, and a flow rate of 1.0 g ml$^{-1}$ hr$^{-1}$, the conversion of DETA

EXAMPLE 4

(a) Preparation of Thorium Silicate Catalyst $Na_2SiO_3 9H_2O$ (284.8 g: 1.00 mole) is added to 1200 ml of water and heated to 80° C. to form a first solution. Concentrated nitric acid (63.0 cc) is added to the first solution slowly, such that no precipitate forms during the addition. The solution is then heated slowly to boiling, and the volume is raised to 2000 ml with water. A second solution is prepared comprising thorium nitrate, $Th(NO_3)_4 \cdot 4H_2O$, (138.4 g: 0.25 mole) and 2000 ml of water, and the solution is heated to boiling. The first solution containing the silicate is added at a rate of 100 cc/min and with rapid stirring to the second solution containing the thorium nitrate. A precipitate forms. The supernatant and the precipitate are heated and stirred for about 3 hours at boiling, and then cooled overnight to room temperature. The precipitate is filtered, washed three times with about 2000 ml of water, and refiltered. The filtercake is dried at 150° C., and calcined at 300° C. overnight to yield a thorium silicate catalyst.

(B) REFORMING OF DIETHYLENETRIAMINE

The thorium silicate catalyst (25.0 g: 8-20 mesh), prepared hereinabove, is placed in a fixed-bed continuous flow reactor. A feedstream comprising diethylenetriamine is passed over the catalyst at a LHSV of about 1.2 g ml$^{-1}$ hr$^{-1}$ and a temperature of 280° C. with the results shown in Table II.

TABLE II

| Ex. 4b [1] | P psig | % DETA Conv. | EDA | TETA (% NC TETA) [3] | TEPA (% NC TEPA) [3] | PEHA | PIP | AEP |
|---|---|---|---|---|---|---|---|---|
| Pass #1 | 1329 | 20 | 5 | 11 (70) | 66 (99) | tr | 14 | 3 |
| Pass #2 | 1364 | 30 | 5 | 13 (60) | 57 (97) | 10 | 12 | 3 |
| Pass #3 | 1346 | 42 | 4 | 16 | 51 | 13 | 12 | 3 |

% Selectivity (DETA-free basis) [2]

TABLE II-continued

| Ex. 4b [1] | P psig | % DETA Conv. | % Selectivity (DETA-free basis) [2] | | | | | |
|---|---|---|---|---|---|---|---|---|
| | | | EDA | TETA (% NC TETA) [3] | TEPA (% NC TEPA) [3] | PEHA | PIP | AEP |
| | | | | (50) | (94) | | | |

[1] Feedstream: Pass #1 employs diethylenetriamine; Pass #2 employs product stream from Pass #1; Pass #3 employs product stream from Pass #2.
[2] % Selectivity is the weight percentage of specific product, based on the total weight of the product stream less the wieght of DETA in the product stream.
[3] (% NC TETA) and (% NC TEPA) represent the weight percentage of triethylenetetramines and tetraethylenepentamines, respectively, which are non-cyclic.

It is seen that thorium silicate catalyzes the reforming of diethylenetriamine to predominantly linearly-extended higher polyethylenepolyamines. The conversion increases with increasing number of passes of the feedstream over the catalyst.

EXAMPLE 5

The thorium silicate catalyst of Example 4(a) is used in the reforming of a mixture of diethylenetriamine and ethylenediamine. The catalyst (25.0 g: 8-20 mesh) is placed in a fixed-bed continuous flow reactor, and the amine mixture is passed over the catalyst at a variety of process conditions with the results shown in Table III.

TABLE III

| EDA/DETA | Temp (°C.) | P psig | LHSV g ml$^{-1}$ hr$^{-1}$ | % DETA Conv. | % Selectivity (EDA-DETA-free basis) [1] | | | | |
|---|---|---|---|---|---|---|---|---|---|
| | | | | | TETA (% NC TETA) [2] | TEPA (% NC TEPA) [2] | PEHA | PIP | AEP |
| 2 | 300 | 1282 | 1.4 | 31 | 43 (88) | 33 (91) | 4 | 14 | 6 |
| 4 | 300 | 1323 | 1.4 | 38 | 56 (95) | 22 (99) | tr | 16 | 6 |
| 4 | 310 | 1241 | 1.3 | 47 | 47 (88) | 27 (88) | 5 | 15 | 7 |

[1] % Selectivity is the weight percentage of specific product, based on the total weight of the product stream less the weight of EDA and DETA in the product stream.
[2] (% NC TETA) and (% NC TEPA) represent the percentage of triethylenetetramines and tetraethylenepentamines, respectively, which are non-cyclic.

It is seen that thorium silicate catalyzes the reforming of mixtures of diethylenetriamine and ethylenediamine to predominantly linearly-extended higher polyethylenepolyamines.

EXAMPLE 6

The thorium silicate catalyst (25.0 g: 80-20 mesh) of Example 4(a) is placed in the reactor of Example 3, and EDA is passed over the catalyst at a LHSV of 1.2 g ml$^{-1}$ hr$^{-1}$, a temperature of 315° C., and a pressure of 1253 psig with the following results: EDA conversion, 36 percent: selectivity (on an EDA-free basis) to DETA, 52 percent: TETA, 24 percent: TEPA, 11 percent: PEHA, 2 percent: PIP, 7 percent; and AEP, 4 percent. The % NC TETA is 88 percent, and the DETA/PIP ratio is 7.4. The % NC TEPA is 84 percent. Thus, thorium silicate catalyzes the reforming of ethylenediamine to predominantly linearly-extended polyethylenepolyamines.

EXAMPLE 7

(a) Preparation of Magnesium Silicate Catalyst

A first solution is prepared by dissolving Na$_2$SiO$_3$.9-H$_2$O (180.0 g: 0.64 mole) in 1200 ml of water and heating to 80° C. Concentrated nitric acid (40.0 ml) is slowly added to the first solution, so that no precipitate forms during the addition. The solution is heated to boiling and the volume is raised to 2000 ml by the addition of water. A second solution is prepared by dissolving Mg(NO$_3$)$_2$.6H$_2$O (81.0 g: 0.32 mole) in 2000 ml of water. The second solution is heated to boiling, whereupon the first solution is added at a rate of 100 ml/min to the second solution with rapid stirring. A precipitate forms. The supernatant and the precipitate are heated and stirred for about 3 hours at boiling, then cooled to room temperature overnight. The precipitate is filtered, washed three times with 2000 ml of water, and refiltered. The filtercake is dried at 100° C. to yield a magnesium silicate catalyst.

(b-c) Reforming of Diethylenetriamine

The magnesium silicate catalyst (25.0 g: 8-20 mesh), prepared in 7(a) hereinabove, is calcined at (b) 300° C. or (c) 550° C. overnight, and then loaded into a fixed-bed continuous flow reactor. A feedstream comprising DETA is passed over the catalyst at a variety of process conditions with the results shown in Table IV.

TABLE IV

| Ex. | Temp (°C.) | P psig | LHSV g ml$^{-1}$ hr$^{-1}$ | % DETA Conv. | % Selectivity (DETA-free-basis) [1] | | | | |
|---|---|---|---|---|---|---|---|---|---|
| | | | | | EDA | TETA (% NC TETA) [2] | TEPA (% NC TEPA) [2] | PEHA | PIP | AEP |
| 7b | 262 | 1182 | 1.3 | 11 | 5 | 14 (53) | 64 (89) | — | 12 | 5 |
| 7b | 280 | 1393 | 3.6 | 19 | 6 | 17 (62) | 51 (97) | 10 | 10 | 6 |
| 7c | 280 | 1399 | 1.2 | 29 | 5 | 15 (51) | 53 (93) | 12 | 11 | 4 |
| 7c | 280 | 1405 | 4.0 | 12 | 6 | 14 (60) | 63 (95) | 1 | 11 | 5 |

TABLE IV-continued

| Ex. | Temp (°C.) | P psig | LHSV g ml$^{-1}$ hr$^{-1}$ | % DETA Conv. | % Selectivity (DETA-free-basis) [1] | | | | | |
|---|---|---|---|---|---|---|---|---|---|---|
| | | | | | EDA | TETA (% NC TETA) [2] | TEPA (% NC TEPA) [2] | PEHA | PIP | AEP |
| 7c | 300 | 1405 | 3.9 | 29 | 6 | 16 (49) | 51 (89) | 13 | 10 | 5 |

[1] % Selectivity is the weight percentage of specific product, based on the total weight of the product stream less the weight of DETA in the product stream.
[2] (% NC TETA) and (% NC TEPA) represent the weight percentage of triethylenetetramines and tetraethylenepentamines, respectively, which are non-cyclic.

It is seen that magnesium silicate catalyzes the reforming of diethylenetriamine to predominantly linearly-extended higher polyethylenepolyamines.

EXAMPLE 8

The magnesium silicate catalyst of Example 7(a) (14.3 g: 8-0 mesh) is calcined at (a) 300° C. or (b) 550° C. overnight. The calcined catalyst is loaded into a fixed-bed continuous flow reactor, and a mixture of diethylenetriamine and athylenediamine in an EDA/DETA mole ratio of 2:1 is passed over the catalyst at a temperature of 280° C. and at the other process conditions shown in Table V.

TABLE V

| Ex. | Pres psig | LHSV g ml$^{-1}$ hr$^{-1}$ | % DETA Conv. | % Selectivity (EDA-DETA-free basis) [1] | | | | |
|---|---|---|---|---|---|---|---|---|
| | | | | TETA (% NC TETA) [2] | TEPA (% NC TEPA) [2] | PEHA | PIP | AEP |
| 8a | 1299 | 1.4 | 31 | 42 (82) | ·32 (85) | 4 | 14 | 5 |
| 8b | 948 | 1.5 | 43 | 36 (73) | 33 (75) | 11 | 12 | 8 |
| 8b | 1200 | 4.0 | 9 | 44 (90) | 32 (99) | tr | 16 | 9 |

[1] Selectivity is the weight percentage of specific product, based on the total weight of the product stream less the weight of EDA and DETA in the product stream.
[2] (% NC TETA) and (% NC TEPA) represent the percentage of triethylenetetramines and tetraethylenepentamines, respectively, which are non-cyclic.

The results in Table V show that magnesium silicate catalyzes the reforming of mixtures of diethylenetriamine and ethylenediamine to predominantly linearly-extended higher polyethylenepolyamines.

EXAMPLE 9

The magnesium silicate catalyst of Example 7(a) (14.3 g; 80-20 mesh) is calcined at 550° C. overnight and then loaded into the reactor of Example 4. Ethylenediamine is passed over the catalyst at a LHSV of 1.4 g ml$^{-1}$ hr$^{-1}$, a temperature of 300° C., and a pressure of 1112 psig with the following results: EDA conversion, 31 percent: selectivity (on an EDA-free basis) to DETA, 53 percent: TETA, 23 percent: TEPA, 11 percent: PEHA, 1 percent: PIP, 7 percent: and AEP, 5 percent. The DETA/PIP ratio is 7.6. The % NC TETA is 79 percent, and the % NC TEPA is 67 percent. Thus, magnesium silicate catalyzes the reforming of ethylenediamine to predominantly linearly-extended higher polyalkylenepolyamines.

What is claimed is:

1. A process of reforming amines comprising contacting an alkyleneamine or mixture thereof with a catalytic amount of a catalyst consisting essentially of a Group IIA metal silicate, with the proviso that the silicate is essentially free of aluminum, the contacting occurring under reaction conditions such that a mixture of polyalkylenepolyamines is formed which is enriched in linearly-extended homologues.

2. The process of claim 1 wherein the alkyleneamine is represented by the formula:

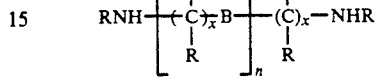

wherein each B is independently NR or O; each R is independently hydrogen, amino, a $C_1$-$C_{12}$ alkyl moiety or $C_1$-$C_{12}$ aminoalkyl moiety, or a monocyclic aryl moiety; each x is independently an integer from 1 to about 12; and n is an integer from 0 to about 150.

3. The process of claim 2 wherein each B is NR and each R is hydrogen.

4. The process of claim 3 wherein the alkyleneamine is ethylenediamine.

5. The process of claim 3 wherein the alkyleneamine is diethylenetriamine.

6. The process of claim 1 wherein the catalyst is magnesium silicate.

7. The process of claim 1 wherein the quantity of catalyst is in the range from about 0.1 weight percent to about 20 weight percent based on the weight of the alkyleneamine reactant.

8. The process of claim 1 wherein the temperature is in the range from about 200° C. to about 400° C.

9. The process of claim 1 wherein the pressure is in the range from about atmospheric to about 4000 psig.

10. The process of claim 1 wherein the liquid hourly space velocity is in the range from about 0.1 g ml$^{-1}$ hr$^{-1}$ to about 10.0 g ml$^{-1}$ hr$^{-1}$.

11. The process of claim 1 wherein the linearly-extended polyalkyleneopolyamines are represented by the formula:

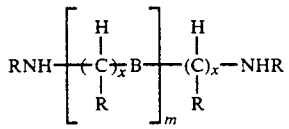

wherein each B is independently NR or O; each R is independently hydrogen, amino, a $C_1$-$C_{12}$ alkyl moiety, a $C_1$–$C_{12}$ aminoalkyl moiety, or a monocyclic aryl moiety; each x is independently an integer from 1 to about 12; and m is an integer from 1 to about 300.

12. The process of claim 11 wherein each R is hydrogen, each B is NR, x is 2, and m is 1, 2, or 3.

13. The process of claim 1 wherein the selectivity for linearly-extended polyalkylenepolyamines is at least about 45 weight percent.

14. The process of claim 13 wherein the selectivity for linearly-extended polyalkylenepolyamines is at least about 75 weight percent.

15. A process of preparing non-cyclic polyethylenepolyamines comprising contacting ethylenediamine, diethylenetriamine or mixtures thereof with a catalyst consisting essentially of magnesium silicate in a continuous flow reactor at a temperature in the range from about 250° C. to about 350° C., a pressure in the range from about 1000 psig to about 2000 psig, an a flow rate from about 0.5 g ml−1 hr−1 to about 5.0 g ml−1 hr−1 such that a mixture of linearly-extended polyethylenepolyamines is formed in a combined selectivity of about 75 weight percent.

16. The process of claim 1 wherein a solvent is employed.

17. The process of claim 1 wherein the Group IIA silicate contains less than about 5 weight percent aluminum.

18. The process of claim 17 wherein the Group IIA silicate contains less than about 2 weight percent aluminum.

19. The process of claim 18 wherein the Group IIA silicate contains less than about 1 weight percent aluminum.

20. The process of claim 6 wherein the silicon to magnesium mole ratio varies from about 0.5 to about 20.

21. The process of claim 15 wherein the weight ratio of diethylenetriamine to piperazine is at least about 3/1.

22. The process of claim 15 wherein the weight percentage of triethylenetetramines which are non-cyclic is at least about 50 weight percent.

23. The process of claim 15 wherein the weight percentage of tetraethylenepentamines which are non-cyclic is at least about 50 weight percent.

* * * * *